United States Patent
Parette et al.

(10) Patent No.: US 10,226,424 B2
(45) Date of Patent: Mar. 12, 2019

(54) THERAPEUTIC CALCIUM PHOSPHATE NANOPARTICLE INCORPORATING SIRNA USEFUL IN TREATING DISEASE

(71) Applicants: Mylisa Parette, Bellefonte, PA (US); Danielle Asquino, Philipsburg, PA (US); Kari Eyer, Sinking Spring, PA (US); James Adair, State College, PA (US); Jeff Davidson, Boalsburg, PA (US); Mark Kester, Harrisburg, PA (US)

(72) Inventors: Mylisa Parette, Bellefonte, PA (US); Danielle Asquino, Philipsburg, PA (US); Kari Eyer, Sinking Spring, PA (US); James Adair, State College, PA (US); Jeff Davidson, Boalsburg, PA (US); Mark Kester, Harrisburg, PA (US)

(*) Notice: Subject to any disclaimer, the term of this patent is extended or adjusted under 35 U.S.C. 154(b) by 249 days.

(21) Appl. No.: 13/964,062

(22) Filed: Aug. 10, 2013

(65) Prior Publication Data

US 2015/0165053 A1    Jun. 18, 2015

Related U.S. Application Data

(60) Provisional application No. 61/682,268, filed on Aug. 12, 2012, provisional application No. 61/799,232, filed on Mar. 15, 2013.

(51) Int. Cl.
| | |
|---|---|
| *A61K 48/00* | (2006.01) |
| *C07H 21/02* | (2006.01) |
| *C07H 21/04* | (2006.01) |
| *A61K 9/14* | (2006.01) |
| *A61K 31/713* | (2006.01) |
| *A61K 31/7105* | (2006.01) |
| *A61K 9/00* | (2006.01) |
| *A61K 47/60* | (2017.01) |
| *A61K 47/69* | (2017.01) |

(52) U.S. Cl.
CPC .............. *A61K 9/14* (2013.01); *A61K 9/0019* (2013.01); *A61K 31/713* (2013.01); *A61K 31/7105* (2013.01); *A61K 47/60* (2017.08); *A61K 47/6923* (2017.08); *Y10T 428/2982* (2015.01)

(58) Field of Classification Search
CPC ............................. A61K 48/00; C12N 15/113
See application file for complete search history.

(56) References Cited

U.S. PATENT DOCUMENTS

| | | | | |
|---|---|---|---|---|
| 2012/0201872 A1* | 8/2012 | Huang et al. | ........... | 424/450 |
| 2015/0157713 A1* | 6/2015 | Peyman | ............ | 514/44 |

FOREIGN PATENT DOCUMENTS

WO    WO 2008/109375 A2 *  9/2008  ........... C12N 15/113

OTHER PUBLICATIONS

Sharma et al., ACS Nano, 2010, 4(3), 1279-1287.*
Receptor-targeted nanocarriers for therapeutic delivery to cancer. Yu B1, Tai HC, Xue W, Lee LJ, Lee RJ.Mol Membr Biol. Oct. 2010;27(7):286-98. doi: 10.3109/09687688.2010.52120.
Nanoparticle-mediated delivery of anticancer agents to tumor angiogenic vessels. Asai T. Biol Pharm Bull. 2012;35(11):1855-61.
Targeting nanoparticles to cancer. Wang M1, Thanou M. Pharmacol Res. Aug. 2010;62(2):90-9. doi: 10.1016/j.phrs.2010.03.005. Epub Apr. 7, 2010.
Bioconjugation of calcium phosphosilicate composite nanoparticles for selective targeting of human breast and pancreatic cancers in vivo.
Barth BM1, Sharma R, Altinoğlu EI, Morgan TT, Shanmugavelandy SS, Kaiser JM, McGovern C, Matters GL, Smith JP, Kester M, Adair JH.
ACS Nano. Mar. 23, 2010;4(3):1279-87. doi: 10.1021/nn901297q.
The ligand nanoparticle conjugation approach for targeted cancer therapy. Karra N1, Benita S. Curr Drug Metab. Jan. 2012;13(1):22-41.
Nucleic acid aptamers: clinical applications and promising new horizons. Ni X1, Castanares M, Mukherjee A, Lupold SE. Curr Med Chem. 2011;18(27):4206-14.
Functionalization of inorganic nanoparticles for bioimaging applications. Erathodiyil N1, Ying JY. Acc Chem Res. Oct. 18, 2011;44(10):925-35. doi: 10.1021/ar2000327. Epub 2011 J.
A comparison of peptide and folate receptor targeting of cancer cells: from single agent to nanoparticle. Franzen S1.
Expert Opin Drug Deliv. Mar. 2011;8(3):281-98. doi: 10.1517/17425247.2011.554816. Epub Feb. 10, 2011.

* cited by examiner

*Primary Examiner* — Amy H Bowman
(74) *Attorney, Agent, or Firm* — Laurence Weinberger

(57) ABSTRACT

Stable, non-toxic, calcium phosphate nanoparticles are formed that incorporate one or more oligonucleotides. RNAi nucleotides may be incorporated and, in particular, siRNA nucleotides. Since the siRNA nanoparticles dissociate leaving only naturally occurring residual materials, calcium and phosphate, along with the siRNA, they are particularly useful as carrier vehicles. The ability to incorporate more than one siRNA provides a means to block or knock down the translation of multiple targeted proteins at the same time.

25 Claims, 10 Drawing Sheets

Specification includes a Sequence Listing.

THERAPEUTIC CALCIUM PHOSPHATE NANOPARTICLE INCORPORATING SIRNA USEFUL IN TREATING DISEASE

Benefit of U.S. Provisional Application No. 61/682,268 filed on Aug. 12, 2012 and U.S. Provisional Application No. 61/799,232 filed on Mar. 15, 2013 is hereby claimed.

GRANT REFERENCE

Some of the work in this invention was made possible with grant support from the National Institutes of Health, National Cancer Institute Contract #HHSN23120100045C. The Government may have certain rights in the invention.

SEQUENCE LISTING

The instant application contains a Sequence Listing which has been submitted electronically in ASCII format and is hereby incorporated by reference in its entirety. Said ASCII copy, created on Mar. 4, 2014, is named 3177-6_SL.txt and is 5,608 bytes in size.

BACKGROUND OF THE INVENTION

Field of the Invention

The present invention describes the formation of stable, non-toxic nanoparticles that incorporate small interfering ribonucleic acids (siRNAs) and a method of using the nanoparticles for systemic treatment of disease.

Background

Many diseases are caused by genetic mutations that lead to abnormal cell function or can be treated by reducing the expression of a targeted gene. In particular, it is believed that a variety of diseases such as genetic, infectious, cardiovascular, metabolic and immune-mediated diseases as well as diabetes, osteoporosis and cancer may be more effectively treated by reducing the expression of specific gene products.

For example, the vast majority of pharmaceutical drugs used to treat cancers utilize unencapsulated free compounds to alter cell function or kill abnormal cells. Virtually all of these treatments utilize non-specific mechanisms of action and have poor biodistribution profiles that result in toxic side effects to healthy tissues. This often occurs from drugs interacting with any cell with which they come in contact, causing significant cell death and toxicity in non-diseased cells. In fact, severe side effects from drugs often limit the dosage that patients can receive. For some diseases, including cancers, this leaves severely ill patients with little choice but to endure widespread toxicity for small gains in therapeutic efficacy.

The elucidation of specific signaling mechanisms and cross-talk between pathways has led to the advent of targeted therapies. These targeted therapies, which interfere with specific molecular pathways, include monoclonal antibodies and small molecule therapeutics. While targeted therapies have improved treatment and survival outcomes, toxic side effects resulting from the inhibition of normal cell function still exist. In addition, infectious organisms and cancerous cells have the ability to "escape" or acquire resistance to therapies by accumulating mutations and altering metabolism during disease progression.

The ability to treat the direct cause of disease, disease-causing genetic mutations, overexpression or infectious agents would provide a therapeutic modality that is only active in the desired cells, providing further specificity that could greatly decrease side effects.

Currently genetic-based therapeutic approaches, including ribonucleic acid interference (RNAi) mediated by small interfering ribonucleic acid (siRNA), are limited by systemic degradation, poor biodistribution and limited cellular uptake. Particularly for systemic administration, the ability to concentrate siRNAs to achieve therapeutic threshold concentrations in the desired tissues remains difficult. Non-toxic nanoscale delivery modalities currently offer the best chance to achieve therapeutic dose levels of siRNA. This is particularly true for cancer applications due to localization of nanoparticles and their associated payloads to solid tumors via the enhanced permeability and retention effect (EPR)[1-3].

Related Art

The design and engineering of siRNA delivery systems has recently been pursued by several groups. Tekmira and Alnylam utilize Solid Nucleic Acid Lipid Nanoparticle (SNALP) technology, which utilizes cationic or charge-conversional lipids with polyethylene glycol (PEG) surface groups, and are currently in early clinical trials[4-10]. The biodistribution of this delivery system mainly targets the liver, limiting the cancer applications and also causing liver toxicity[11].

Calando has developed a cyclodextrin-based delivery system which has proven immunogenic in early clinical trials and difficult to manufacture[12-15].

Silence Therapeutics AtuPlex lipid-based delivery system is currently undergoing early clinical studies[16-19].

Several academic groups have explored the use of calcium phosphate nanoparticles for siRNA delivery[20-31]. However, these methods do not teach the synthesis of calcium phosphate-siRNA nanoparticles that do not include other, potentially toxic components, such as residual buffers (Tris & HEPES) or synthesis components (surfactants). From a pharmaceutical standpoint, toxicity can be a limiting factor to drug development and eliminating potential toxicity through the exclusion of unnecessary components has been a goal not previously achieved in designing a drug delivery system.

Each of the prior art approaches to produce calcium phosphate nanoparticles for siRNA delivery has run into a problem. For example, Epple et al teaches the use of siRNA as the dispersant. It has been noted that doing so will likely compromise dispersion in vivo[28]. Huang et al, utilizes a difficult to purify microemulsion system as well as cationic lipids for dispersion[20,21,24,25,30,31], which will limit biodistribution. The microemulsion synthesis also involves materials known to be toxic that may be incorporated into the resulting nanoparticles. Kataoka et al, employs exotic and potentially toxic charge conversional block co-polymers[26,27] for dispersion. In addition, Kataoka's particles are precipitated in the presence of buffers such as HEPES and Tris[22,23,26-29]. Tris is known to be a toxic compound, therefore the association of these molecules with the calcium phosphate nanoparticles can be expected to cause toxicity. None of the above referenced groups has shown a detailed molecular analysis of their particles to demonstrate the lack of incorporation of residual, toxic components.

Another approach was explored by a group at the University of Tokyo that used double stranded siRNA conjugated to PEG via a disulfide bond to provide dispersion[29]. As shown in that work[29], as well as work done by the present inventors, the particle architecture resulting from Zhang's method is colloidally unstable, particularly in the presence of serum, and therefore not suitable for therapeutic development.

DEFINITION

"siRNA NanoJackets" shall mean calcium phosphate nanoparticles incorporating siRNA made in accordance with the teachings in this patent disclosure.

BRIEF DESCRIPTION OF THE DRAWINGS

FIG. 1A shows particle architecture of a siRNA NanoJacket using phosphoamide conjugation chemistry. The siRNA-PEG conjugate merges into a calcium phosphate core particle via the available 5'$PO_4$ group. PEG groups are oriented towards the solution phase. FIG. 1B shows the chemical structure of siRNA-PEG conjugate with phosphoamide chemistry. The phosphoamide bond attaches a 5' phosphate on the sense strand of the siRNA to an amine terminal group on a 2K amine-PEG-methoxy molecule. FIG. 1C shows the chemical structure of siRNA-PEG conjugate with thioether chemistry.

FIG. 2A depicts the dependence of siRNA concentration on the formation of a siRNA NanoJackets using a 25-bp siRNA with the phosphoamide conjugation chemistry. High (130 uM), mid (120 uM) and low (110 uM) represent different concentrations of siRNA added during the synthesis. The highest concentration shows multi-modal peaks indicating disparate particle formation, the mid concentration shows a monomodal particle distribution while the lowest concentration shows multi-modal peaks including large (>1 um) aggregates. FIG. 2B depicts size dependence of siRNA concentration on the formation of siRNA NanoJackets using a 21-bp siRNA with phosphoamide conjugation chemistry. The addition of increasing siRNA-PEG conjugate concentrations results in decreasing particle size.

FIG. 2A As measured by dynamic light scattering, particle size distribution is shown, for siRNA NanoJackets synthesized with 21-bp siRNA using the phosphoamide chemistry. The insert is an image of the particles using transmission electron microscopy. FIG. 2B As measured by dynamic light scattering, particle size distribution is shown for siRNA NanoJackets synthesized with a different 21-bp siRNA using the phosphoamide chemistry including cryo-transmission electron microscopy (inset).

FIG. 5A shows three independent measurements of the Zeta potential of a single-sequence siRNA NanoJacket containing a 21-bp siRNA using the thioether conjugation chemistry. A mean zeta potential was measured as −30.3 mV. FIG. 5B shows the Zeta potential of a single target-sequence siRNA NanoJacket containing 21-bp siRNA using the phosphoamide conjugation chemistry. The NanoJacket shows a mean zeta potential of −30.1 mV when unmodified (black line) and −21.1 mV after incubation with 2 mM $CaCl_2$ at 37 C for one hour (gray line).

FIG. 9A shows the effect of treating female SCID mice harboring subcutaneous human MCF7 breast cancer tumors with siRNA NanoJackets containing an active siRNA sequence targeting the PI3KCA 1633 G>A mutation (group1), siRNA NanoJackets containing the inactive, Scramble sequence (group 2) or a dextrose control solution via intravenous administration twice weekly for 5 weeks followed by a week of recovery. Doses of siRNA NanoJackets increased during the treatment course from 2 mg/kg for the first two weeks to 6 mg/kg for the second two weeks to 10 mg/kg for the fifth week. FIG. 9B shows the effect of treating female SCID CB-17 mice harboring orthotopic HCC1954 breast cancer tumors with siRNA NanoJackets containing an active siRNA sequence (group1), siRNA NanoJackets containing an inactive, scramble sequence (group 2) or a dextrose control solution via intravenous administration at 2.5 mg/kg siRNA three times weekly for 4 weeks. The body weights of mice treated with siRNA NanoJackets did not significantly differ from those treated with a control, dextrose solution.

DETAILED DESCRIPTION OF THE INVENTION

Figure 1:
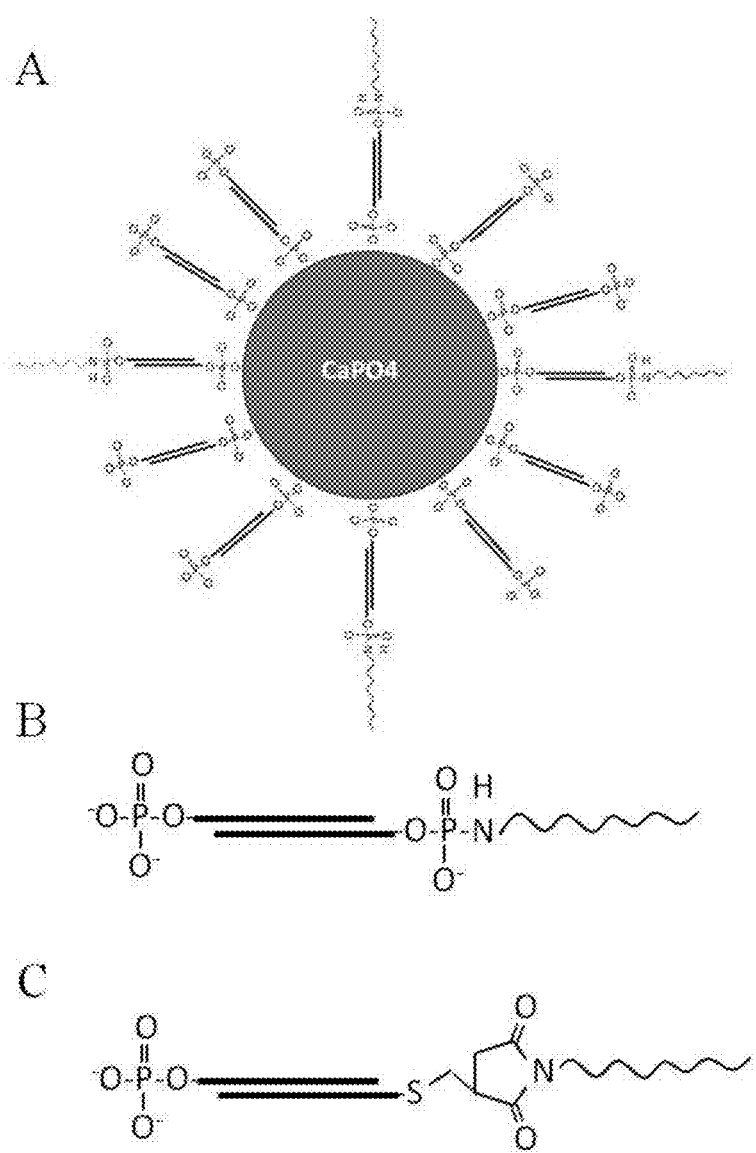
FIG. 1 is a cartoon of siRNA-PEG conjugates and siRNA NanoJacket structure.

Ribonucleic acid interference (RNAi), has the ability to directly treat genetic mutations by blocking the translation of targeted proteins[31-33]. This occurs when a small interfering ribonucleic acid (siRNA), typically 19- to 25-base pairs in length and designed to bind to an mRNA that codes for a specific protein, is delivered intracellularly, associates with the RISC complex in the cytoplasm and then binds to the corresponding mRNA in the cells, preventing protein translation. siRNA is designed to target and knockdown a specific protein by using a complimentary base sequence to the mRNA of the desired protein. In this manner, the use of siRNA to mediate RNAi can prevent the translation of the encoded protein. For point mutations that result in hyperactivation of signaling pathways and cell growth, RNAi can be utilized as a potent and specific therapeutic. However, the ability to effectively deliver siRNA molecules for treatment has proven challenging. Particularly for systemic administration, the ability to concentrate siRNA to achieve therapeutic threshold concentrations in primary sites of disease and, in the case of cancer, in metastasized tumor sites, following systemic administration has been difficult.

This patent document teaches the formation of stable non-toxic calcium phosphate nanoparticles incorporating siRNA with or without polyethylene glycol (PEG) as a terminal surface group. The nanoparticles may be employed for the purpose of systemic therapeutic administration of siRNA. Calcium and phosphate are used to create the nanoparticle matrix while PEG is included as it provides steric protection from both aggregation and immune system clearance during circulation. The described nanoparticles increase the therapeutic efficacy of the incorporated siRNA by: 1) protecting the siRNA oligonucleotide from degradation during circulation; 2) extending the circulation time; 3) concentrating the siRNA in solid tumor sites via the enhanced permeability and retention effect; and 4) allowing the addition of active targeting moieties such as peptides, antibodies or aptamers to the terminal PEG motifs. By increasing the concentration of siRNA in disease sites, knockdown of the target protein(s) is more completely achieved than by prior art approaches and results in decreased cell growth and/or death. The increased efficacy that results as well as the absence of nanomaterial-mediated toxicity of the siRNA nanoparticle provide a novel therapeutic mechanism for the treatment of cancer and other diseases. Preferably, the disease or tumor will be characterized prior to treatment to allow the intelligent design or selection of therapeutic siRNA targets. The calcium phosphate siRNA nanotherapeutics may be administered alone or as part of a treatment regimen including other tumor therapies.

Key distinguishing characteristics of the described siRNA nanoparticles include: 1) the use of 5' $PO_4$ groups on the siRNA to facilitate binding with the calcium phosphate nanoparticle; 2) the use of phosphoamide or thioether chemistry to facilitate the stable attachment of PEG in the presence of serum, 3) the ability to determine nanoparticle size by the control of component concentrations in the synthesis process; 4) the overall simplicity of the particle formation; 5) the lack of cationic dispersants resulting in negative surface charge; and 5) exclusion of potentially toxic components such as lipid-based compounds.

The present invention significantly advances the state of the art of siRNA nanoparticles that provides a new pathway for therapeutic siRNA delivery. Due to the specificity of RNAi, this invention provides a unique nanoparticle and enables an advanced method for the treatment of cancer and other diseases where siRNA may be employed. At the same time, nanoparticles of this invention reduce the toxic side effects compared to conventional or targeted treatments while inhibiting disease processes due to over-expressed or hyperactive proteins.

Methods of Nanoparticle Fabrication

Calcium phosphate siRNA NanoJackets are created by the addition of $CaCl_2$, $Na_2HPO_4$, and a combination of siRNA and PEG-conjugated siRNA (FIG. 1).

Formation of PEG-Conjugated siRNA Duplexes:

This patent document sets forth the use of thioether and phosphoamide conjugations to link the siRNA and PEG as examples of appropriate linking chemistries. However, those skilled in the art will understand that any number of alternate conjugation chemistries may be used and are considered within the teachings of this patent document. Further, as will also be appreciated by those skilled in the art, the invention is not limited to the disclosed examples of siRNA, but provides for the use of other siRNAs which are selected for a specific target sequence. Likewise, those skilled in the art will also appreciate that other oligonucleotides, such as microRNA (miRNA), or fragments of messenger RNA (mRNA) or deoxyribonucleic acid (DNA), in a substantially similar size range, may be used with this invention.

The initial stages of synthesis involve the conjugation of 21- or 25-base pair siRNA to PEG moieties. The phosphoamide chemistry involves conjugating siRNA with 5' $PO_4$ end groups to an amine-terminated methoxy PEG molecule (FIG. 1B), while the thioether chemistry involves conjugating siRNA with 5'-sulfhydryl end groups to a maleimide-terminated methoxy PEG molecule (FIG. 1C). To achieve the phosphoamide conjugation, 0.12M N-(3-Dimethylaminopropyl)-N'-ethylcarbodiimide hydrochloride, 47.6 uM single stranded siRNA (inactive strand containing 5' $PO_4$ groups) and 0.238M amine-PEG are dissolved in 0.1M imidazole at pH 6 and incubated 18 hrs at 50 C. This reaction typically yields 15-30% conjugation. Alternatively, the addition of 0.1M MES buffer, pH 4, into the phosphoamide reaction mixture results in conjugation efficiency of 75-90%. For the thioether chemistry, 200 uM single stranded siRNA (inactive strand containing 5' $PO_4$ groups) is combined with 0.476M amine-PEG in the presence of 0.02M DTT in a 0.1M Tris HCl buffer and the reaction is incubated at 25 C 18 hrs. This reaction yields approximately 50% conjugation. These reactions have been performed using 2 kDa and 5 kDa PEG molecules. Following conjugation, the inactive (sense) strand is annealed to the unconjugated active (antisense) strand RNA in the reaction mix by heating to 70 C followed by slow cooling. For the highly efficient (75-90%) phosphoamide reaction, unconjugated, annealed siRNA containing either 5'$PO_4$ groups on both the active (antisense) and inactive (sense) strand or one 5' $PO_4$ group on the active (antisense) strand are added to the reaction mixture to facilitate desalt purification, as described below. The presence of 5' $PO_4$ groups on the inactive (sense) strand results in a more negatively charged particle while the absence of these groups shifts the particle charge closer to neutral.

Purification is achieved using a modified desalting procedure that is carried out by combining 1 volume of annealed conjugation reaction mixture, 1 volume of 5M sodium acetate and 13 parts 70:30 ethyl acetate:methanol. Following incubation at −80 C for at least 18 hours, the mixture is centrifuge for 90 minutes at 21,000 g and 4 C, the supernatant is decanted. A second desalt with methanol follows the above procedure and pellets are washed with 80% methanol and then dried. This procedure facilitates the separation of both the free and conjugated siRNA from excess PEG and reaction components including imidazole, carbodiimide, DTT, Tris and most salts.

Formation of siRNA NanoJackets:

To form siRNA NanoJackets, the conjugated siRNA as prepared above is added to $Na_2HPO_4$ in aqueous solution. The solution is then mixed with $CaCl_2$ that has been adjusted to pH 8.5-10.5, most optimally pH 9. A final molar ratio of calcium to phosphate between 0.9-1.5:1, most optimally 1.2:1 is required to form stable particles. Optimal component concentrations are 5 mM $Na_2HPO_4$, 4.05 mM $CaCl_2$ and 80 uM-225 uM siRNA. However, the siRNA concentration may be varied depending on the sequence and length of sequence. Shorter, 21-bp siRNA duplexes, typically require higher concentrations of approximately 175-225 uM siRNA to stabilize a monomodal particle size distribution, while longer siRNA duplexes, 25-bp, require less material, typically approximately 80-125 uM siRNA to yield the same particle size. Some variation in particle size distribution about the lower and higher siRNA concentrations is seen between sequences of the same length. Higher siRNA concentrations are required to attain monomodal particle size distributions of <250 nm if the inactive (sense) strand does not contain 5' $PO_4$ groups.

Particles are washed via centrifuge filtration with 5% dextrose containing calcium and phosphate to remove unincorporated siRNA and siRNA-PEG conjugates. Alternatively, unincorporated siRNA, Ca, Cl, Na and $PO_4$ can be removed from the suspension by ultracentrifugation at 132,000 g, which results in particle collection in the bottom 10% of the sample volume. Separation of the bottom 10% of the sample volume containing the particles reduces residual unincorporated components by up to 90%. Capture of the siRNA within the particle is sequence dependent and ranges from 10-25% of the siRNA added in the synthesis. The synthesis describe herein results in calcium phosphate nanoparticles containing siRNA with monomodal particle size distributions of ≤160 nm, as shown below.

Modification of Surface Charge:

Modification of the surface charge after particle formation and purification can be achieved by incubating the particles in 1-10 mM $CaCl_2$ at 37 C for 1-24 hours. The incubation at elevated temperature is required to bind Ca to the siRNA. This binding is not seen when similar amounts of $CaCl_2$ are added to the particles at room temperature. This modification of surface charge is employed to affect the efficiency of cellular uptake of the particles that ultimately influences therapeutic efficacy.

Of particular note in the described synthesis of the siRNA nanoparticle is the absence of HEPES, Tris or other buffers during particle synthesis that have been utilized for prior art calcium phosphate siRNA nanoparticle syntheses[22,23,26-29]. These components, while required for pH control in the published synthetic processes, are toxic and, if incorporated into the particle, may result in detrimental off-target toxicities. Also absent from the present synthesis are lipids or any cationic dispersants that could mediate accumulation in the liver after systemic administration. As described, the siRNA NanoJackets of the present invention are synthesized with only water, $CaCl_2$, $Na_2HPO_4$, siRNA and siRNA-PEG conjugates that leave only Na and Cl as non-toxic, residual counter ions. The simplicity of the disclosed synthetic design that not only excludes potentially toxic components but also provides the ability to finely control particle size by controlling concentrations within the synthetic process differentiates siRNA NanoJackets of the present invention from prior art nanoparticles described in the literature and patents.

Figure 2:
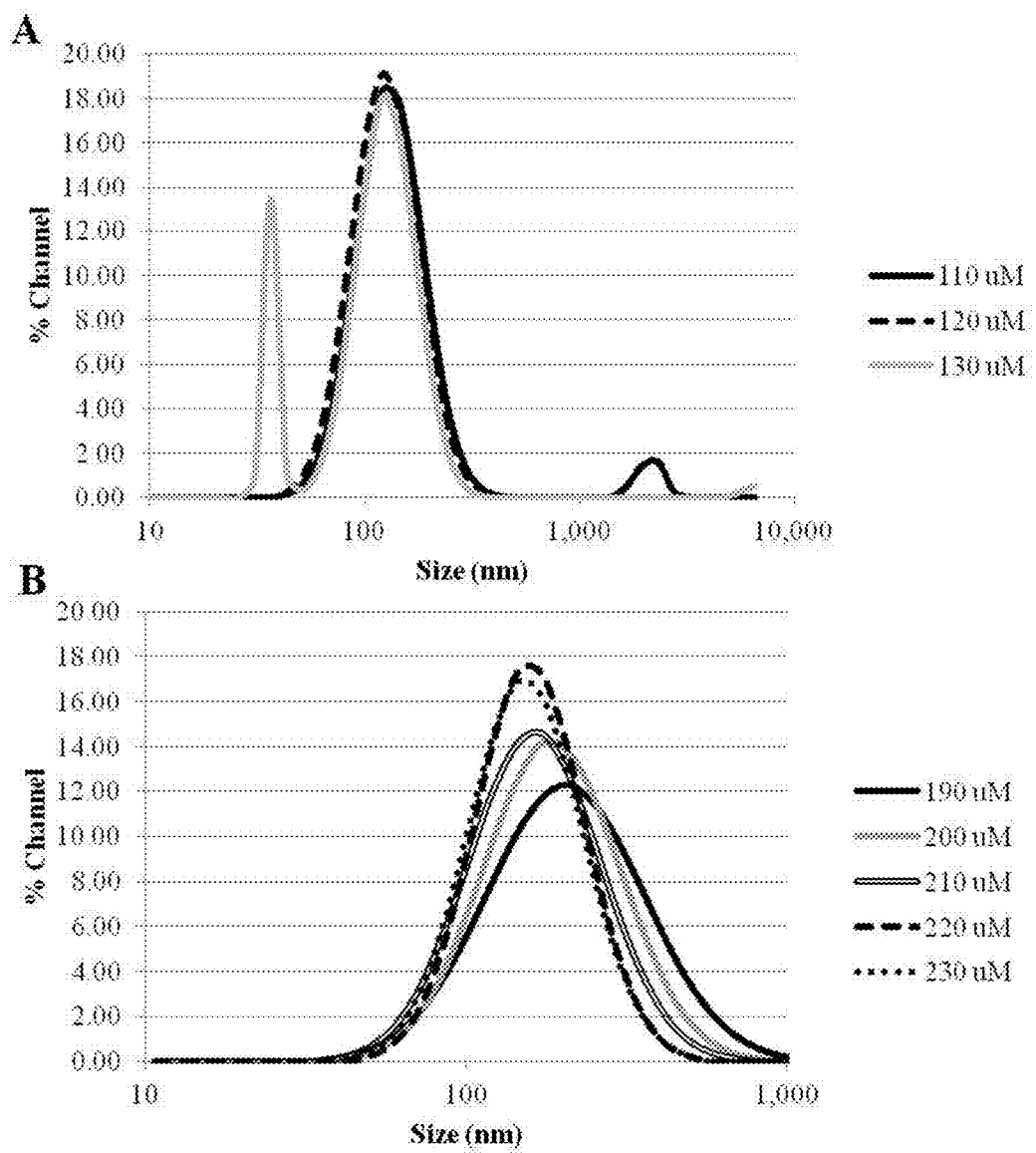
FIG. 2 demonstrates NanoJacket formation and size based on siRNA concentration.
Figure 3:
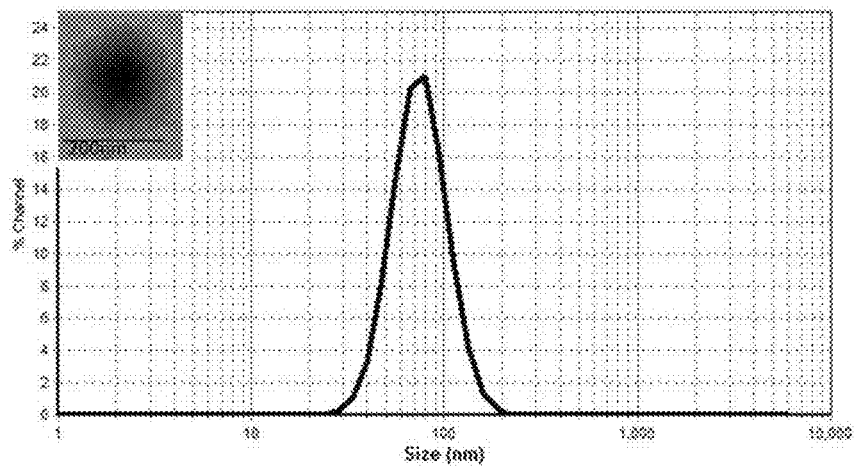
FIG. 3 demonstrates the particle morphology and size distribution obtained for single target sequence siRNA NanoJacket.
Figure 3:
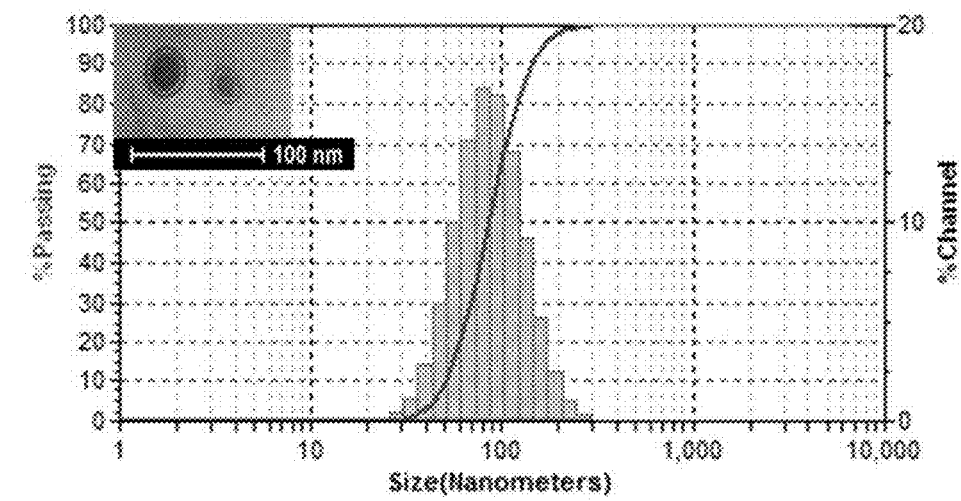

The size of siRNA NanoJackets, within a specified concentration range and molar ratio of calcium and phosphate, is controlled via the concentrations of siRNA-PEG added in the synthesis (FIG. 2). The siRNA-PEG conjugates mediate dispersion via both charge due to the negative phosphate groups on the siRNA as well as steric hindrance due to the elongated PEG molecules. The concentrations required for the formation of stable particles falls within a range that encompasses enough siRNA to provide dispersion while not overwhelming the system by preventing particle precipitation. This optimal concentration range differs with oligonucleotide size. For 25 bp siRNAs, the optimal concentration range is between 80-125 uM, while for 21 bp siRNAs, the optimal concentration range is between 175-225 uM. The siRNA sequence, presumably due to secondary structure, also has an effect as the preferred concentration for different siRNA sequences varies within the indicated ranges. Since siRNA that will be employed will vary depending on the target sequence selected, no absolute concentration can be taught. However, for those familiar with and skilled in the art, it is very simple and straight forward to determine the preferred concentration of any given siRNA. The preferred concentration for a particular siRNA sequence is determined by experimentally varying the siRNA concentration within the indicated range and analyzing the resulting particles to determine the concentration that provides the smallest, monomodal particle size distribution. Within the taught concentration ranges, higher amounts of siRNA during synthesis result in decreased particle size. The resulting siRNA NanoJackets have a mean hydrodynamic diameter between 90-160 nm when created using a single siRNA sequence (FIG. 3).

The method described in this patent document to form siRNA NanoJackets provides significant versatility in the range of siRNA that may be incorporated. As noted above, microRNA as well as longer oligonucleotides may be used. To demonstrate the broad range and applicability of siRNA NanoJacket formation, examples of 11 different siRNA sequences that have been introduced into siRNA NanoJackets are presented, consisting of 21- and 25-base pair duplexes with standard phosphoamidite backbone chemistry with or without 2' O-methoxy base modifications. siRNAs containing both blunt ends as well as 3' nucleotide overhangs are included. 2'O-methoxy modified base are denoted by m. siRNA sequences used to demonstrate siRNA Nano-Jacket formation include:

```
PI3K CA-
Active-5'-AUCGAUAAGCUGUCGCACGGUUAGA-  (SEQ ID NO: 1)
3'
Inactive-5'-UCUAACCGUGCGACAGCUUAUC   (SEQ ID NO: 2)
GAG-3'
Preferred concentration-100 uM
PI3KCA-3140 A > G mutation
Active-5'-AAAUGAAUGAUGCACGUCAUGGUGG- (SEQ ID NO: 3)
3'
Inactive-5'-ACCAUGACGUGCAUCAUUCAUU   (SEQ ID NO: 4)
UGU-3'
Preferred concentration-100 uM
PI3KCA-3140 A > G mutation
Active-5'-GUCAUGGUGGCUGGACAACAA-3'   (SEQ ID NO: 5)
Inactive-5'-GmUmUGmUCCAGCCACCAmUGAA  (SEQ ID NO: 6)
GmU-3'
Preferred concentration-200 uM
PI3KCA-1633 G > A mutation
Active-5'-CUCUCUGAAAUCACUAAGCUU-3'   (SEQ ID NO: 7)
Inactive-5'-GCUUAGUGAUUUCAGAGAUUU-3' (SEQ ID NO: 8)
Preferred concentration-200 uM
PI3KCA-333 G > C mutation
Active-5'-CAACCGUGAAGAAAACAUCUU-3'   (SEQ ID NO: 9)
Inactive-5'-GAUGUUUUCUUCACGGUAGUU-3' (SEQ ID NO: 10)
Preferred concentration-225 uM
```

-continued

```
HER2 (as published 34)-
Active-5'-UCUCUGCGGUGGUUGGCAUUC-3'      (SEQ ID NO: 11)
Inactive-5'-ACCAUGACGUGCAUCAUUCAUU      (SEQ ID NO: 12)
UGU-3'
Preferred concentration-200 uM
HER2-
Active-5'-UUCCGAAAGAGCUGGUCCCUU-3'      (SEQ ID NO: 13)
Inactive-5'-GGGACCAGCmUCmUmUmUCGGAAm    (SEQ ID NO: 14)
UmU-3'
Preferred concentration-175 uM
PLK (as published35)-
Active-5'-UAUUUAAmGGAGGGUGAmUCUUU-3'    (SEQ ID NO: 15)
Inactive-5'-AGAmUCACCCmUCCUmUAAAmU      (SEQ ID NO: 16)
AUU-3'
Luciferase (as published35)-
Active-5'-UACAmUAACCGGACAmUAAmUCUU-     (SEQ ID NO: 17)
3'
Inactive-5'-GAmUUAmUGmUCCGGmUmUA-       (SEQ ID NO: 18)
mUGmU
AUU
Preferred concentration-200 uM
BRAF-V600E mutation (as published36)-
Active-5'-GGUCUAGCUACAGAGAAAUCUCGAU-    (SEQ ID NO: 19)
3'
Inactive-5'-CGAGAUUUCUCUGUAGCUAGAC      (SEQ ID NO: 20)
CAU-3'
Preferred concentration-100 uM
Scramble (as published36)-
Active-5'-AAUUCUCCGAACGUGUCACGUGAGA-    (SEQ ID NO: 21)
3'
Inactive-5'-UCUCACGUGACACGUUCGGAGA      (SEQ ID NO: 22)
AUU-3'
Preferred concentration-100 uM
```

Figure 4:
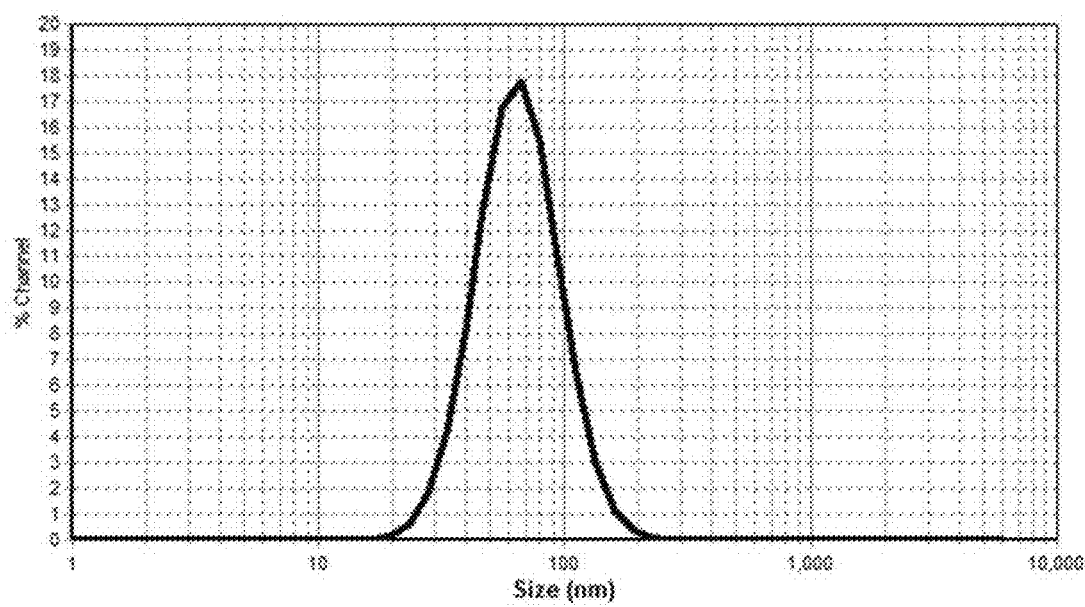
FIG. 4 shows the particle size distribution, as measured by dynamic light scattering, of siRNA NanoJackets containing two different 25-bp siRNA sequences using the phosphoamide chemistry. In the preparation of these particles, both siRNA sequences were added in equal amounts to form the siRNA NanoJackets.
Figure 5:
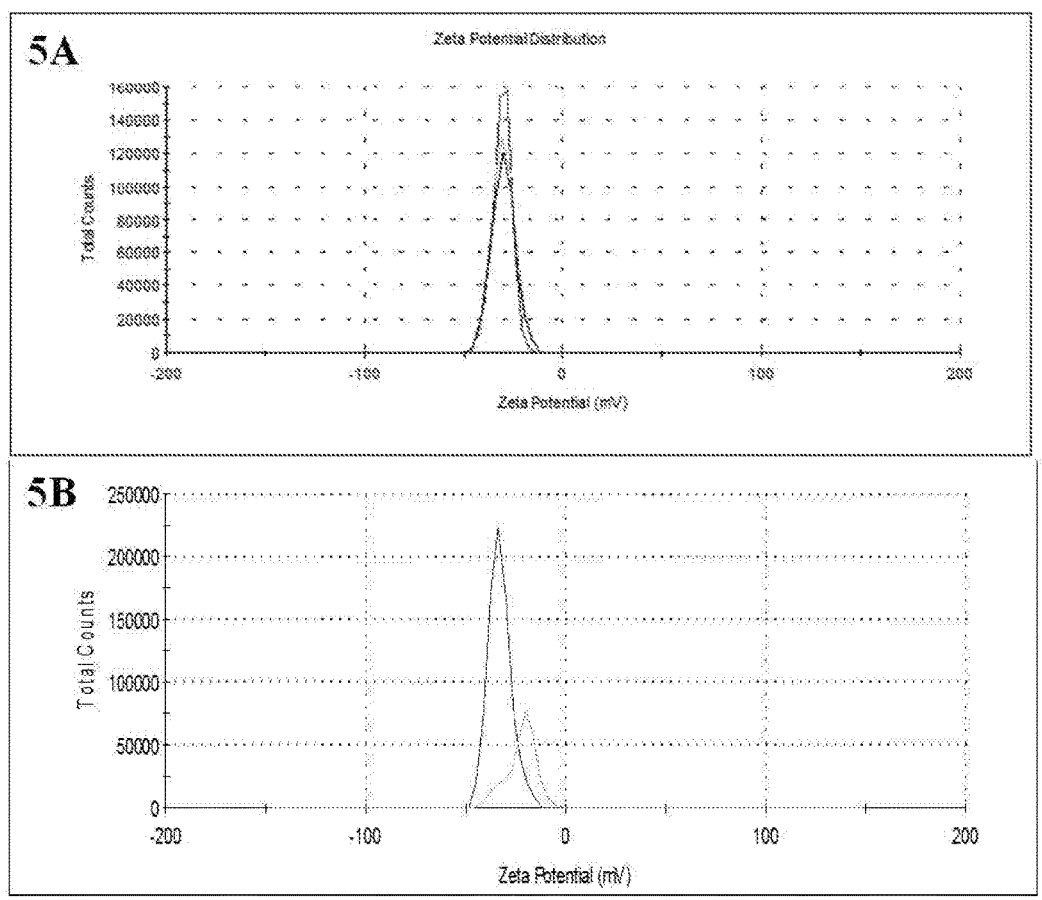
FIG. 5 shows the Zeta potential distribution, as measured by quasi-electric light scattering.

Particle size distributions of the nanoparticles incorporating the above specified siRNAs are monomodal, and the size distributions have been corroborated by TEM measurements (FIG. 3). The particles show a distinct core-shell structure and correlate with the particle size distribution as measured by dynamic light scattering (DLS). In addition to single-sequence particles, siRNA NanoJackets have been synthesized including two different siRNA sequences, PI3KCA and HER2 (FIG. 4). This is a significant advance over nanoparticles taught in the prior art. The ratio of each sequence of siRNA in the siRNA nanoparticle is controlled during synthesis by the amount of each siRNA added prior to particle formation. Thus, the siRNA NanoJackets of the present invention can be created using multiple siRNA sequences directed against different target proteins. Therefore, the method of the invention produces siRNA NanoJackets with the ability to reduce the expression of multiple proteins in exact proportion to the proportion of siRNAs incorporated with each NanoJacket for multi-therapeutic delivery. This achievement enables multiple components of cellular pathways to, for instance, be disrupted to increase efficacy and eliminate resistance mechanisms. siRNA NanoJackets harboring ~15-30% PEG groups on the terminal particle surface have a negative surface charge of ~−30 mV, as indicated by zeta potential measurements (FIG. 5A). Further modification of the particle charge by the addition of calcium, as described above, shifts the zeta potential to be less negative (FIG. 5B). This reduced negative surface charge is in contrast to many cationic lipid and polymer systems and will reduce uptake by non-tumor cells due to the lack of ionic attraction to negatively charged cell membranes. siRNA NanoJackets containing 15-30% PEG conjugated with phosphoamide chemistry with the remainder of siRNA having 5'$PO_4$ groups on both the inactive and active strands have a zeta potential of approximately −30.98+/−2.44 mV. After synthesis and purification, incubation of siRNA NanoJackets in 1 mM, 1.5 mM or 2 mM $CaCl_2$ results in zeta potentials of −26.98+/−1.36 mV, −22.94+/−0.87 mV and −21.12+/−0.50 mV, respectively.

Figure 6:
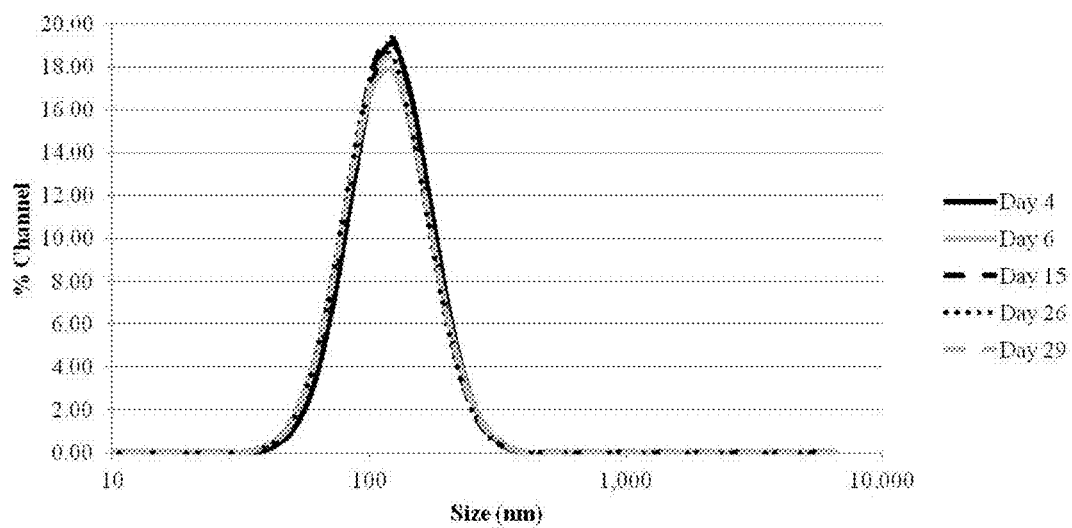
FIG. 6 shows the particle size distributions over time of single-sequence siRNA NanoJackets containing a 25-bp siRNA using the phosphoamide conjugation chemistry to demonstrate the NanoJackets stability. Measurements taken on days 4, 6, 15, 26 and 29 post-synthesis indicate siRNA NanoJackets are stable for at least 29 days FIG. 7 demonstrates that siRNA NanoJackets are stable for extended times when incubated in the presence of serum. Single-sequence siRNA NanoJackets containing a 25-bp siRNA using the (A) phosphoamide or (B) thioether conjugation chemistries were incubated in RPMI cell culture media with 10% fetal bovine serum (FBS). Particle size distributions using heterodyne light scattering were measured at the indicated time points. Particle size distributions from the RPMI with FBS background were subtracted out to isolate NanoJacket distributions. siRNA NanoJackets retained the primary particle size distribution for at least 48 hours days when incubated at ambient temperature and at least 4 days when incubated at 37 C.

The synthetic method described in this patent document results in nanoparticles that are stable for at least 29 days as demonstrated in FIG. 6.

Figure 7:
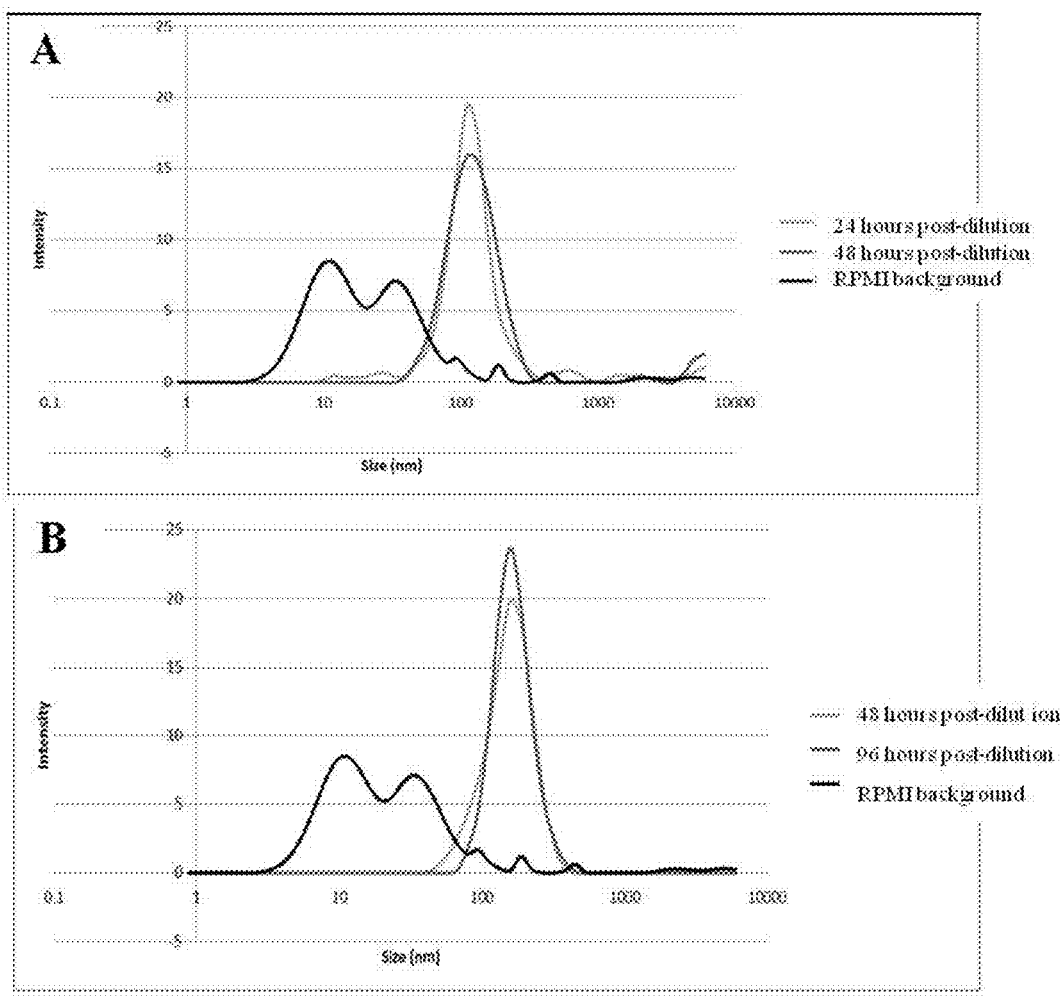

The siRNA nanoparticles particles described are stable in the presence of serum, as demonstrated by particle size distribution measurements on both thioether (FIG. 7A) and phosphoamide (FIG. 7B) siRNA NanoJackets incubated in cell culture media with 10% fetal bovine serum. The lack of larger particle sizes, which would show aggregation or complete reduction of peak intensity, indicates that the nanoparticles remain unchanged during incubation in serum, and thus are stable under these conditions. This feature is in contrast to previously published data on calcium phosphate siRNA particles that utilized disulfide siRNA-PEG linkages that were found to be unstable in the presence of serum[29]. Simply tweaking or adjusting the teachings of the prior art with respect to siRNA nanoparticle formation does not result in nanoparticles that are stable and able to deliver siRNA in vitro or in vivo. The enabling features of utilizing phosphoamide and thioether conjugation chemistries, as well as conjugating 15-30% of the siRNA and excluding potentially toxic compounds and buffers from the synthetic process has enabled safe systemic administration of these particles and therefore their use as therapeutic agents.

Figure 8:
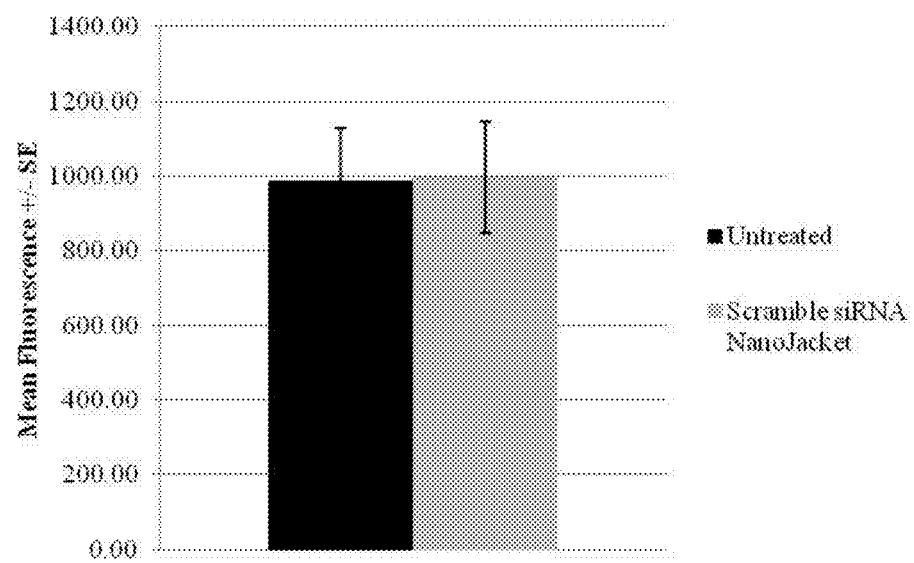
FIG. 8 demonstrates that siRNA NanoJackets are non-toxic in vitro. MDA-MB-453 breast cancer cells were treated with either media or siRNA NanoJackets containing a 25-bp scramble sequence using the phosphoamide chemistry. Cellular viability was measured via a fluorescent Cell Titer Blue assay to determine cellular respiration. The siRNA NanoJacket treatment at 2.5 uM of siRNA did not decrease cellular respiration following 72 hours of treatment.
Figure 9:
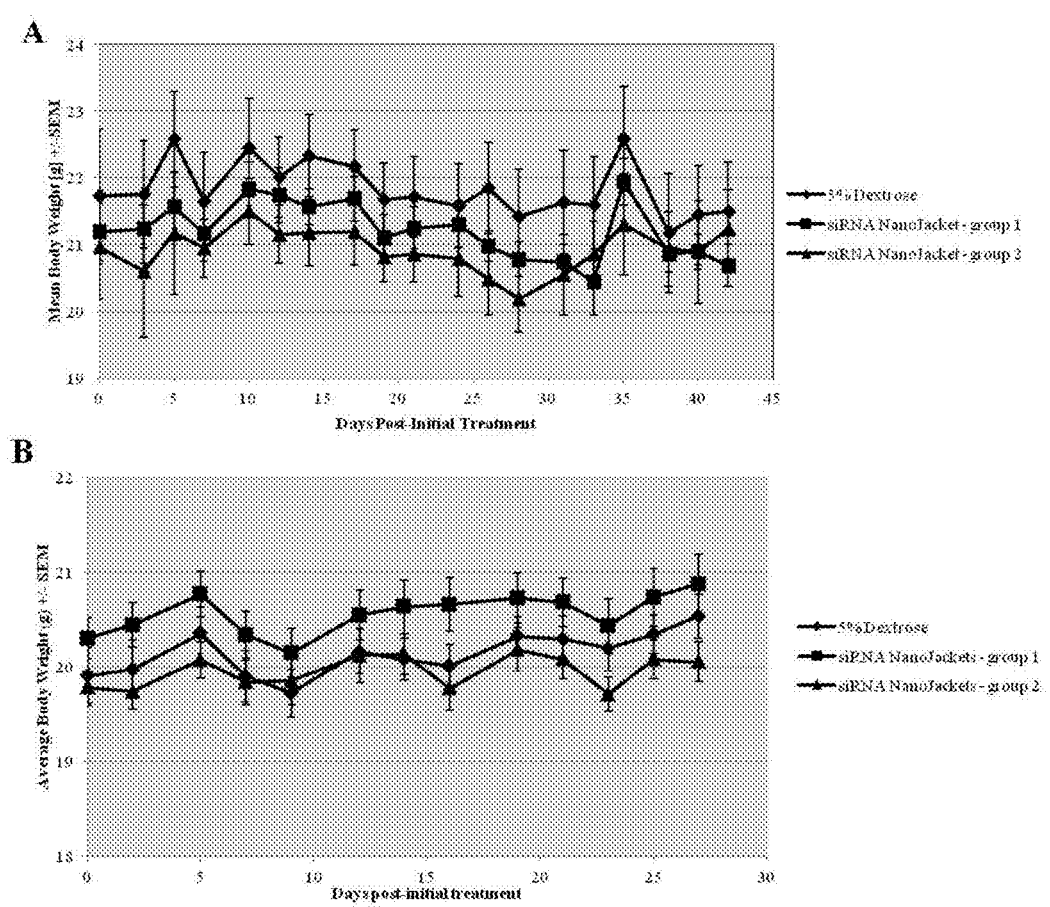
FIG. 9 demonstrates that treatment with siRNA NanoJackets had no effect on body weight (a measure of toxicity).

The lack of toxicity of siRNA NanoJackets has been demonstrated both in vitro and in vivo. Treatment of cells incorporating scrambled siRNA sequences result in no toxicity in vitro (FIG. 8). Since the scrambled siRNA does not affect any specific proteins, the only component left that might be toxic is the NanoJacket. The absence of any toxicity thus indicates that the delivery vehicle itself is not toxic. In addition, intravenous administration of siRNA NanoJackets to mice twice per week at escalating dosages (2 weeks @ 2 mg/kg, 2 weeks @ 6 mg/kg, 1 week at 10 mg/kg) resulted in no clinical signs of toxicity or significant changes in body weight over the course of 5 weeks of treatment (FIG. 9). The experimental data provides further indication that even at high and repeated dosages, siRNA NanoJackets harboring both active siRNA or inactive control siRNA sequences are not toxic.

Figure 10:
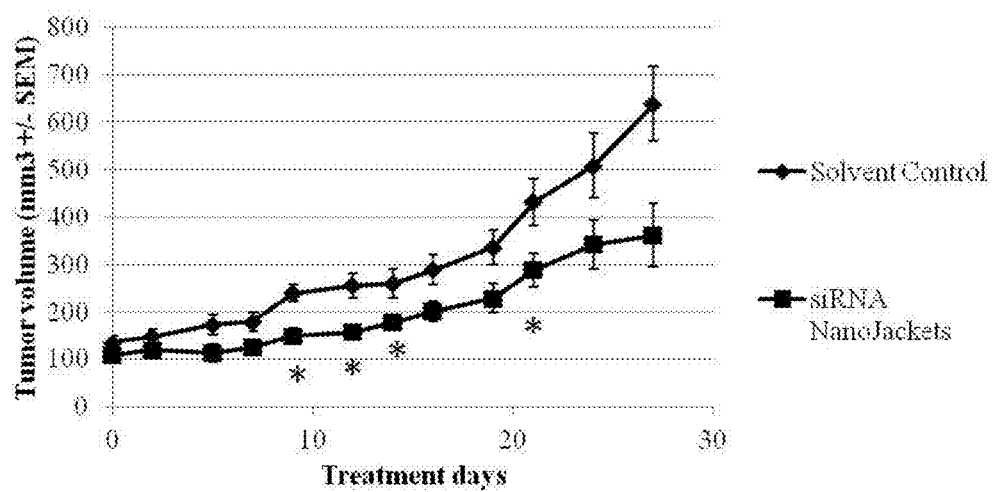
FIG. 10 demonstrates the efficacy of siRNA NanoJackets against human breast cancer tumors. Orthotopic HCC1954, human breast cancer tumors were established in SCID-CB17 mice. The mice were treated three times weekly with i.v. administrations of solvent (5% dextrose) or siRNA NanoJackets (2.5 mg/kg). The siRNA was directed against two different cancer-causing mutations within the HCC1954 tumors. Tumor volume is shown as the median tumor volume+/−standard error. *=p<0.05

Evidence of the utility of siRNA NanoJackets to mediate successful delivery of siRNAs to tumor cells after systemic treatment is shown in FIG. 10. When administered intravenously three times per week at a dose of 2.5 mg/kg of siRNA, siRNA NanoJackets carrying sequences targeting HER2 and PI3KCA 3140A>G demonstrated significant efficacy against HCC1954 human breast cancer cells as shown by the reduction in tumor volume.

Methods of siRNA NanoJacket Use siRNA NanoJackets are intended as a therapeutic to treat disease. Since the NanoJackets dissociate leaving only naturally occurring residual materials, calcium and phosphate, they are particularly useful for carrier vehicles. Based on the composition of the siRNA NanoJackets, it is expected that siRNA NanoJackets will be intravenously administered to patients at a therapeutic dosage to achieve treatment for a disease. Alternate routes of administration may include topical, oral buccal, subcutaneous and intramuscular.

SYNTHETIC EXAMPLES

Example 1—Method for Synthesizing siRNA NanoJackets Using 21 bp siRNA that is not Conjugated to PEG Using nuclease free water, 32 mM $CaCl_2$, 24 mM $Na_2HPO_4$ and 500 uM double stranded siRNA are prepared by reconstituting the components to the specified concentrations. Concentrations of the $CaCl_2$ and $Na_2HPO_4$ solutions are verified by conductivity measurements and adjusted, as necessary. Small errors in solution concentration can cause variation in particle size distribution and aggregation of the resulting nanoparticles. The measurement of conductivity is a good way to refine the concentration of the solutions as it directly measures ions in solution. Refining the concentration of solutions used for nanoparticle synthesis results in reproducible production of nanoparticles. All solutions are adjusted to pH 10, which also increases reproducibility of the resulting nanoparticles, using NaOH and the concentrations are recalculated accounting for the volume of NaOH added. The solutions are further diluted with nuclease free water and the following solutions are combined: 10 uL 400 uM double stranded siRNA, 3.3 uL of 30 mM $CaCl_2$ and 6.7 uL 12.1 mM $Na_2HPO_4$ to achieve final concentrations of 200 uM siRNA, 5 mM $CaCl_2$ and 4.05 mM $Na_2HPO_4$. The sample is vortexed to mix, both between additions and when all solutions are combined. siRNA NanoJackets are allowed to mature at ambient temperature (20-25 C) for 18 hours. To concentrate and purify siRNA NanoJackets from unincorporated siRNA and siRNA-PEG, the siRNA NanoJacket solution is ultracentrifuged at 132,000 g for 30 minutes at ambient temperature. The top 90% of solution is removed, taking care not to disturb the bottom 10%. The bottom 10% is collected and mixed to homogenize the solution. If modification of surface charge is desired, purified NanoJackets are combined with $CaCl_2$ adjusted to pH 10 with NaOH, to obtain a final concentration of 2 mM of the added $CaCl_2$. The solution is incubated at 37 C for 1-24 hours, most optimally 3 hours.

Example 2—Method for Synthesizing siRNA NanoJackets Using 25 bp siRNA that is not Conjugated to PEG Using nuclease free water, 32 mM $CaCl_2$, 24 mM $Na_2HPO_4$ and 500 uM double stranded siRNA are prepared by reconstituting the components to the specified concentrations. Concentrations of the $CaCl_2$ and $Na_2HPO_4$ solutions are verified by conductivity measurements and adjusted, as necessary. Small errors in solution concentration can cause variation in particle size distribution and aggregation of the resulting nanoparticles. The measurement of conductivity is a good way to refine the concentration of the solutions as it directly measures ions in solution. Refining the concentration of solutions used for nanoparticle synthesis results in reproducible production of nanoparticles. All solutions are adjusted to pH 10, which also increases reproducibility of the resulting nanoparticles, using NaOH and the concentrations are recalculated accounting for the volume of NaOH added. The solutions are further diluted with nuclease free water and the following solutions are combined: 5 uL 400 uM double stranded siRNA, 3.3 uL of 30 mM $CaCl_2$ and 11.7 uL of 6.9 mM $Na_2HPO_4$ to achieve final concentrations of 100 uM siRNA, 5 mM $CaCl_2$ and 4.05 mM $Na_2HPO_4$. The sample is vortexed to mix, both between additions and when all solutions are combined. siRNA NanoJackets are allowed to mature at ambient temperature (20-25 C) for 18 hours. To concentrate and purify siRNA NanoJackets from unincorporated siRNA and siRNA-PEG, the siRNA NanoJacket solution is ultracentrifuged at 132,000 g for 30 minutes at ambient temperature. The top 90% of solution is removed, taking care not to disturb the bottom 10%. The bottom 10% is collected and mixed to homogenize the solution. If modification of surface charge is desired, purified NanoJackets are combined with $CaCl_2$ adjusted to pH 10 with NaOH, to obtain a final concentration of 2 mM of the added $CaCl_2$. The solution is incubated at 37 C for 1-24 hours, most optimally 3 hours.

Example 3—Method for Synthesizing siRNA NanoJackets that Utilize a Thioether Bond Between 21 or 25 bp siRNA and a 2 kDa PEG The following reactants are combined: 100 uL 500M double stranded siRNA with one 5' phosphate group and the other 5' thiol group, 10 uL 1M DTT, 50 uL 1M Tris and 340 uL 0.7M 2 kDa mPEG-maleimide. The reactants are vortexed to mix and then incubated at ambient temperature (20-25 C) for 18 hours to allow the conjugation reaction to occur. Following incubation, conjugation efficiency is confirmed by agarose gel electrophoresis. To purify the conjugation reaction, 1 mL of the reaction is added to 1 mL 5M sodium acetate and 13 mLs 200 proof methanol. After vortexing to mix, the solution is held at −80 C overnight. The solution is centrifuged at 15,000 g at 4 C for 90 minutes after which a pellet is formed and the supernatant is decanted. The pellet is washed with 4 parts ice cold 80% methanol and held at −80 C for one hour and then centrifuged at 15,000 g at 4 C for 45 minutes to form a pellet. After the supernatant is decanted, the pellet is dried by speed vac and resuspended to 500 uM siRNA in nuclease free water. Recovery is determined by $Abs_{260}$ and the ratio of conjugated to unconjugated siRNA is determined by agarose gel electrophoresis. This reaction typically results in ~25% conjugation efficiency. Using nuclease free water, 32 mM $CaCl_2$, 24 mM $Na_2HPO_4$ are prepared. Concentrations of the $CaCl_2$ and $Na_2HPO_4$ solutions are verified by conductivity measurements and adjusted, as necessary. Small errors in solution concentration can cause variation in particle size distribution and aggregation of the resulting nanoparticles. The measurement of conductivity is a good way to refine the concentration of the solutions as it directly measures ions in solution. Refining the concentration of solutions used for nanoparticle synthesis results in reproducible production of nanoparticles. All solutions, including siRNA, are adjusted to pH 10, which also increases reproducibility of the resulting nanoparticles, using NaOH and the concentrations are recalculated accounting for the volume of NaOH added. The solutions are further diluted with nuclease free water to achieve the desired concentrations, as follows. For 25 bp siRNAs the following solutions are combined: 5 uL 400 uM double stranded siRNA, 3.3 uL of 30 mM $CaCl_2$ and 11.7 uL of 6.9 mM $Na_2HPO_4$ to achieve final concentrations of 100 uM siRNA, 5 mM $CaCl_2$ and 4.05 mM $Na_2HPO_4$. For 21 bp siRNAs, the following solutions are combined: 10 uL 400 uM double stranded siRNA, 3.3 uL of 30 mM $CaCl_2$ and 6.7 uL 12.1 mM $Na_2HPO_4$ to achieve final concentrations of 200 uM siRNA, 5 mM $CaCl_2$ and 4.05 mM $Na_2HPO_4$. The sample is vortexed to mix, both between additions and when all solutions are combined. siRNA NanoJackets are allowed to mature at ambient temperature (20-25 C) for 18 hours. To concentrate and purify siRNA NanoJackets from unincorporated siRNA and siRNA-PEG, the siRNA NanoJacket solution is ultracentrifuged at 132,000 g for 30 minutes at ambient temperature. The top 90% of solution is removed, taking care not to disturb the bottom 10%. The bottom 10% is collected and mixed to homogenize the solution. If modification of surface charge is desired, purified NanoJackets are combined with $CaCl_2$ adjusted to pH 10 with NaOH, to obtain a final concentration of 2 mM of the added CaCl$_2$. The solution is incubated at 37 C for 1-24 hours, most optimally 3 hours.

Example 4—Method for Synthesizing siRNA NanoJackets that Utilize a Thioether Bond Between 21 or 25 bp siRNA and a 5 kDa PEG The following reactants are combined: 100 uL 500M double stranded siRNA with one 5' phosphate group and the other 5' thiol group, 10 uL 1M DTT, 50 uL 1M Tris and 340 uL 0.2M 2 kDa mPEG-maleimide. The reactants are vortexed to mix and then incubated at ambient temperature (20-25 C) for 18 hours to allow the conjugation reaction to occur. Following incubation, conjugation efficiency is confirmed by agarose gel electrophoresis. To purify the conjugation reaction, 1 mL of the reaction is added to 1 mL 5M sodium acetate and 13 mLs 70/30 v/o ethyl acetate/methanol. After vortexing to mix, the solution is held at −80 C overnight. The solution is centrifuged at 15,000 g at 4 C for 90 minutes after which a pellet is formed. After the supernatant is decanted, the pellet is dried by speed vac and resuspended to 500 uM siRNA in nuclease free water. A second purification is performed by the addition of 100 uL resuspended pellet to 100 uL 5M sodium acetate and 1300 uL 200 proof methanol. After vortexing to mix, the solution is held at −80 C overnight. The solution is centrifuged at 21,000 g at 4 C for 90 minutes after which a pellet is formed and the supernatant is decanted. The pellet is washed with 4 parts ice cold 80% methanol and held at −80 C for one hour and then centrifuged at 21,000 g at 4 C for 45 minutes to form a pellet. After the supernatant is decanted, the pellet is dried by speed vac and resuspended to 500 uM siRNA in nuclease free water. Recovery is determined by Abs$_{260}$ and the ratio of conjugated to unconjugated siRNA is determined by agarose gel electrophoresis. This reaction typically results in ~25% conjugation efficiency. Using nuclease free water, 32 mM CaCl$_2$, 24 mM Na$_2$HPO$_4$ are prepared. Concentrations of the CaCl$_2$ and Na$_2$HPO$_4$ solutions are verified by conductivity measurements and adjusted, as necessary. Small errors in solution concentration can cause variation in particle size distribution and aggregation of the resulting nanoparticles. The measurement of conductivity is a good way to refine the concentration of the solutions as it directly measures ions in solution. Refining the concentration of solutions used for nanoparticle synthesis results in reproducible production of nanoparticles. All solutions, including siRNA, are adjusted to pH 10, which also increases reproducibility of the resulting nanoparticles, using NaOH and the concentrations are recalculated accounting for the volume of NaOH added. The solutions are further diluted with nuclease free water to achieve the desired concentrations, as follows. For 25 bp siRNAs the following solutions are combined: 5 uL 400 uM double stranded siRNA, 3.3 uL of 30 mM CaCl$_2$ and 11.7 uL of 6.9 mM Na$_2$HPO$_4$ to achieve final concentrations of 100 uM siRNA, 5 mM CaCl$_2$ and 4.05 mM Na$_2$HPO$_4$. For 21 bp siRNAs, the following solutions are combined: 10 uL 400 uM double stranded siRNA, 3.3 uL of 30 mM CaCl$_2$ and 6.7 uL 12.1 mM Na$_2$HPO$_4$ to achieve final concentrations of 200 uM siRNA, 5 mM CaCl$_2$ and 4.05 mM Na$_2$HPO$_4$. The sample is vortexed to mix, both between additions and when all solutions are combined. siRNA NanoJackets are allowed to mature at ambient temperature (20-25 C) for 18 hours. To concentrate and purify siRNA NanoJackets from unincorporated siRNA and siRNA-PEG, the siRNA NanoJacket solution is ultracentrifuged at 132,000 g for 30 minutes at ambient temperature. The top 90% of solution is removed, taking care not to disturb the bottom 10%. The bottom 10% is collected and mixed to homogenize the solution. If modification of surface charge is desired, purified Nano-Jackets are combined with CaCl$_2$ adjusted to pH 10 with NaOH, to obtain a final concentration of 2 mM of the added CaCl$_2$. The solution is incubated at 37 C for 1-24 hours, most optimally 3 hours.

Example 5—Method for Synthesizing siRNA NanoJackets that Utilize a Phosphoamide Bond Between 21 or 25 bp siRNA and a 2 kDa PEG The following reactants are combined: 15 mg EDC is resuspended in 50 uL 1 mM single stranded RNA with a 5' phosphate group and then added to 1,000 uL 0.25M 2 kDa mPEG-NH2 in 0.1M imidazole HCl, pH 6. The reactants are vortexed to mix and then incubated at 50 C for 18 hours in a dry heat block to allow the conjugation reaction to occur. The single stranded RNA is then annealed by the addition of 50 uL of 1 mM of the complimentary single stranded RNA containing a 5' phosphate group. The solution is vortexed to mix and then incubated at above the melting point of the duplex, for example 70 C, for 20 minutes and then allowed to cool slowly back to ambient temperature. Following annealing, conjugation efficiency is confirmed by agarose gel electrophoresis. To purify the conjugation reaction, 1 mL of the reaction is added to 1 mL 5M sodium acetate and 13 mL 200 proof methanol. After vortexing to mix, the solution is held at −80 C overnight. The solution is centrifuged at 15,000 g at 4 C for 90 minutes after which a pellet is formed and the supernatant is decanted. The pellet is washed with 4 parts ice cold 80% methanol and held at −80 C for one hour and then centrifuged at 15,000 g at 4 C for 45 minutes to form a pellet. After the supernatant is decanted, the pellet is dried by speed vac and resuspended to 500 uM siRNA in nuclease free water. Recovery is determined by Abs$_{260}$ and the ratio of conjugated to unconjugated siRNA is determined by agarose gel electrophoresis. This reaction typically results in ~25% conjugation efficiency. Using nuclease free water, 32 mM CaCl$_2$, 24 mM Na$_2$HPO$_4$ are prepared. Concentrations of the CaCl$_2$ and Na$_2$HPO$_4$ solutions are verified by conductivity measurements and adjusted, as necessary. Small errors in solution concentration can cause variation in particle size distribution and aggregation of the resulting nanoparticles. The measurement of conductivity is a good way to refine the concentration of the solutions as it directly measures ions in solution. Refining the concentration of solutions used for nanoparticle synthesis results in reproducible production of nanoparticles. All solutions, including siRNA, are adjusted to pH 10, which also increases reproducibility of the resulting nanoparticles, using NaOH and the concentrations are recalculated accounting for the volume of NaOH added. The solutions are further diluted with nuclease free water to achieve the desired concentrations, as follows. For 25 bp siRNAs the following solutions are combined: 5 uL 400 uM double stranded siRNA, 3.3 uL of 30 mM CaCl$_2$ and 11.7 uL of 6.9 mM Na$_2$HPO$_4$ to achieve final concentrations of 100 uM siRNA, 5 mM CaCl$_2$ and 4.05 mM Na$_2$HPO$_4$. For 21 bp siRNAs, the following solutions are combined: 10 uL 400 uM double stranded siRNA, 3.3 uL of 30 mM CaCl$_2$ and 6.7 uL 12.1 mM Na$_2$HPO$_4$ to achieve final concentrations of 200 uM siRNA, 5 mM CaCl$_2$ and 4.05 mM Na$_2$HPO$_4$. The sample is vortexed to mix, both between additions and when all solutions are combined. siRNA NanoJackets are allowed to mature at ambient temperature (20-25 C) for 18 hours. To concentrate and purify siRNA NanoJackets from unincorporated siRNA and siRNA-PEG, the siRNA NanoJacket solution is ultracentrifuged at 132,000 g for 30 minutes at ambient temperature. The top 90% of solution is removed, taking care not to disturb the bottom 10%. The bottom 10% is collected and mixed to homogenize the solution. If modification of surface charge is desired, purified NanoJackets are combined with $CaCl_2$ adjusted to pH 10 with NaOH, to obtain a final concentration of 2 mM of the added $CaCl_2$. The solution is incubated at 37 C for 1-24 hours, most optimally 3 hours.

Example 6—Method for Synthesizing siRNA NanoJackets that Utilize a Phosphoamide Bond Between 21 or 25 bp siRNA and a 5 kDa PEG The following reactants are combined: 15 mg EDC is resuspended in 105 uL MES buffer, pH 4, followed by addition of 50 uL 1 mM single stranded RNA with a 5' phosphate group and 895 uL 0.15M 5 kDa mPEG-NH2 in 0.172M imidazole HCl, pH 6. The reactants are vortexed to mix and then incubated at 50 C for 18 hours in a dry heat block to allow the conjugation reaction to occur. The single stranded RNA is then annealed by the addition of 50 uL of 1 mM of the complimentary single stranded RNA containing a 5' phosphate group. The solution is vortexed to mix and then incubated at above the melting point of the duplex, for example 70 C, for 20 minutes and then allowed to cool slowly back to ambient temperature. Following annealing, conjugation efficiency is confirmed by agarose gel electrophoresis. To purify the conjugation reaction, 1 mL of the reaction is added to 1 mL 5M sodium acetate and 13 mLs 70/30 v/o ethyl acetate/methanol. After vortexing to mix, the solution is held at −80 C overnight. The solution is centrifuged at 15,000 g at 4 C for 90 minutes after which a pellet is formed. After the supernatant is decanted, the pellet is dried by speed vac and resuspended to 500 uM siRNA in nuclease free water. A second purification is performed by the addition of 100 uL resuspended pellet to 100 uL 5M sodium acetate and 1300 uL 200 proof methanol. After vortexing to mix, the solution is held at −80 C overnight. The solution is centrifuged at 21,000 g at 4 C for 90 minutes after which a pellet is formed and the supernatant is decanted. The pellet is washed with 4 parts ice cold 80% methanol and held at −80 C for one hour and then centrifuged at 21,000 g at 4 C for 45 minutes to form a pellet. After the supernatant is decanted, the pellet is dried by speed vac and resuspended to 500 uM siRNA in nuclease free water. Recovery is determined by $Abs_{260}$ and the ratio of conjugated to unconjugated siRNA is determined by agarose gel electrophoresis. This reaction typically results in ~25% conjugation efficiency. Using nuclease free water, 32 mM $CaCl_2$, 24 mM $Na_2HPO_4$ are prepared. Concentrations of the $CaCl_2$ and $Na_2HPO_4$ solutions are verified by conductivity measurements and adjusted, as necessary. Small errors in solution concentration can cause variation in particle size distribution and aggregation of the resulting nanoparticles. The measurement of conductivity is a good way to refine the concentration of the solutions as it directly measures ions in solution. Refining the concentration of solutions used for nanoparticle synthesis results in reproducible production of nanoparticles. All solutions, including siRNA, are adjusted to pH 10, which also increases reproducibility of the resulting nanoparticles, using NaOH and the concentrations are recalculated accounting for the volume of NaOH added. The solutions are further diluted with nuclease free water to achieve the desired concentrations, as follows. For 25 bp siRNAs the following solutions are combined: 5 uL 400 uM double stranded siRNA, 3.3 uL of 30 mM $CaCl_2$ and 11.7 uL of 6.9 mM $Na_2HPO_4$ to achieve final concentrations of 100 uM siRNA, 5 mM $CaCl_2$ and 4.05 mM $Na_2HPO_4$. For 21 bp siRNAs, the following solutions are combined: 10 uL 400 uM double stranded siRNA, 3.3 uL of 30 mM $CaCl_2$ and 6.7 uL 12.1 mM $Na_2HPO_4$ to achieve final concentrations of 200 uM siRNA, 5 mM $CaCl_2$ and 4.05 mM $Na_2HPO_4$. The sample is vortexed to mix, both between additions and when all solutions are combined. siRNA NanoJackets are allowed to mature at ambient temperature (20-25 C) for 18 hours. To concentrate and purify siRNA NanoJackets from unincorporated siRNA and siRNA-PEG, the siRNA NanoJacket solution is ultracentrifuged at 132,000 g for 30 minutes at ambient temperature. The top 90% of solution is removed, taking care not to disturb the bottom 10%. The bottom 10% is collected and mixed to homogenize the solution. If modification of surface charge is desired, purified NanoJackets are combined with $CaCl_2$ adjusted to pH 10 with NaOH, to obtain a final concentration of 2 mM of the added $CaCl_2$. The solution is incubated at 37 C for 1-24 hours, most optimally 3 hours.

Example 7—Method for Synthesizing siRNA NanoJackets that Utilize a Phosphoamide Bond Between 21 or 25 bp siRNA and a 2 kDa PEG and Achieve Up to 75% Conjugation The following reactants are combined: 15 mg EDC is resuspended in 105 uL MES buffer, pH 4, followed by addition of 315 uL nuclease free water, 50 uL 1 mM single stranded RNA with a 5' phosphate group and 580 uL 0.431M 2 kDa mPEG-NH2 in 0.172M imidazole HCl, pH 6. The reactants are vortexed to mix and then incubated at 50 C for 18 hours in a dry heat block to allow the conjugation reaction to occur. The single stranded RNA is then annealed by the addition of 50 uL of 1 mM of the complimentary single stranded RNA containing a 5' phosphate group. The solution is vortexed to mix and then incubated at above the melting point of the duplex, for example 70 C, for 20 minutes and then allowed to cool slowly back to ambient temperature. Following annealing, conjugation efficiency is confirmed by agarose gel electrophoresis. This reaction typically produces ~75% conjugation efficiency. To adjust the percentage of PEG within the NanoJacket, unconjugated double stranded siRNA containing two 5' phosphate groups is added in the desired ratio. To purify the conjugation reaction, 1 mL of the reaction is added to 1 mL 5M sodium acetate and 13 mLs 70/30 v/o ethyl acetate/methanol. After vortexing to mix, the solution is held at −80 C overnight. The solution is centrifuged at 15,000 g at 4 C for 90 minutes after which a pellet is formed. After the supernatant is decanted, the pellet is dried by speed vac and resuspended to 500 uM siRNA in nuclease free water. A second purification is performed by the addition of 100 uL resuspended pellet to 100 uL 5M sodium acetate and 1300 uL 200 proof methanol. After vortexing to mix, the solution is held at −80 C overnight. The solution is centrifuged at 21,000 g at 4 C for 90 minutes after which a pellet is formed and the supernatant is decanted. The pellet is washed with 4 parts ice cold 80% methanol and held at −80 C for one hour and then centrifuged at 21,000 g at 4 C for 45 minutes to form a pellet. After the supernatant is decanted, the pellet is dried by speed vac and resuspended to 500 uM siRNA in nuclease free water. Recovery is determined by $Abs_{260}$ and the ratio of conjugated to unconjugated siRNA is determined by agarose gel electrophoresis. Using nuclease free water, 32 mM $CaCl_2$, 24 mM Na$_2$HPO$_4$ are prepared. Concentrations of the CaCl$_2$ and Na$_2$HPO$_4$ solutions are verified by conductivity measurements and adjusted, as necessary. Small errors in solution concentration can cause variation in particle size distribution and aggregation of the resulting nanoparticles. The measurement of conductivity is a good way to refine the concentration of the solutions as it directly measures ions in solution. Refining the concentration of solutions used for nanoparticle synthesis results in reproducible production of nanoparticles. All solutions, including siRNA, are adjusted to pH 10, which also increases reproducibility of the resulting nanoparticles, using NaOH and the concentrations are recalculated accounting for the volume of NaOH added. The solutions are further diluted with nuclease free water to achieve the desired concentrations, as follows. For 25 bp siRNAs the following solutions are combined: 5 uL 400 uM double stranded siRNA, 3.3 uL of 30 mM CaCl$_2$ and 11.7 uL of 6.9 mM Na$_2$HPO$_4$ to achieve final concentrations of 100 uM siRNA, 5 mM CaCl$_2$ and 4.05 mM Na$_2$HPO$_4$. For 21 bp siRNAs, the following solutions are combined: 10 uL 400 uM double stranded siRNA, 3.3 uL of 30 mM CaCl$_2$ and 6.7 uL 12.1 mM Na$_2$HPO$_4$ to achieve final concentrations of 200 uM siRNA, 5 mM CaCl$_2$ and 4.05 mM Na$_2$HPO$_4$. The sample is vortexed to mix, both between additions and when all solutions are combined. siRNA NanoJackets are allowed to mature at ambient temperature (20-25 C) for 18 hours. To concentrate and purify siRNA NanoJackets from unincorporated siRNA and siRNA-PEG, the siRNA NanoJacket solution is ultracentrifuged at 132,000 g for 30 minutes at ambient temperature. The top 90% of solution is removed, taking care not to disturb the bottom 10%. The bottom 10% is collected and mixed to homogenize the solution. If modification of surface charge is desired, purified NanoJackets are combined with CaCl$_2$ adjusted to pH 10 with NaOH, to obtain a final concentration of 2 mM of the added CaCl$_2$. The solution is incubated at 37 C for 1-24 hours, most optimally 3 hours.

REFERENCES

1. Maeda, H. Tumor-selective delivery of macromolecular drugs via the EPR effect: background and future prospects. *Bioconjug Chem* 21, 797-802.
2. Matsumura, Y. & Maeda, H. A new concept for macromolecular therapeutics in cancer chemotherapy: mechanism of tumoritropic accumulation of proteins and the antitumor agent smancs. *Cancer Res* 46, 6387-6392 (1986).
3. Skinner, S. A., Tutton, P. J. & O'Brien, P. E. Microvascular architecture of experimental colon tumors in the rat. *Cancer Res* 50, 2411-2417 (1990).
4. Alsina, M., Tabernero, J., Shapiro, G., Burris, H., Infante, J R., Weiss, G J., Cervantes-Ruiperez, A., Gounder, M M., Paz-Ares, L., Falzone, R., Hill, J., Cehelsky, J., Vaishnaw, A., Gollob, J., LoRusso, P. Open-label extension study of the RNAi therapeutic ALN-VSP02 in cancer patients responding to therapy. *Journal of Clinical Oncology* 30, suppl; abstract 3062 (2012).
5. Cervantes, A., Alsina, M., Tabernero, J., Infante, J R., LoRusso, P., Shapiro, G., Paz-Ares, L G., Falzone, R., Hill, J., Cehelsky, J., White, A., Roudjarska, I., Bumcrot, D., Meyers, R., Hinkle, G., Svrzikapa, N., Sah, D W., Vaishnaw, A., Gollob, J., Burris, H A. Phase I dose-escalation study of ALN-VSP02, a novel RNAi therapeutic for solid tumors with liver involvement. *Journal of Clinical Oncology* 29, suppl; abstract 3025 (2011).
6. DeVincenzo, J., et al. A randomized, double-blind, placebo-controlled study of an RNAi-based therapy directed against respiratory syncytial virus. *Proc Natl Acad Sci USA* 107, 8800-8805.
7. Gollob, J., Infante, G., Shapiro, P., LoRusso, B., Dezube, B J., Heymach, J., Cehelsky, J., Falzone, R., Vaishnaw, A., Burris, H A. Interim safety and pharmacodynamic results for ALN-VSP02, a novel RNAi therapeutic for solid tumors with liver involvement. *Journal of Clinical Oncology* 28:15s, supp; abstract 3042 (2010).
8. Love, K. T., et al. Lipid-like materials for low-dose, in vivo gene silencing. *Proc Natl Acad Sci USA* 107, 1864-1869.
9. Semple, S. C., et al. Rational design of cationic lipids for siRNA delivery. *Nat Biotechnol* 28, 172-176.
10. Zimmermann, T. S., et al. RNAi-mediated gene silencing in non-human primates. *Nature* 441, 111-114 (2006).
11. Alnylam. Phase I Dose Escalation Study of ALN-VSP02—A Novel RNAi Therapeutic for Solid Tumors with Liver Involvement. (2011).
12. Bartlett, D. W., Su, H., Hildebrandt, I. J., Weber, W. A. & Davis, M. E. Impact of tumor-specific targeting on the biodistribution and efficacy of siRNA nanoparticles measured by multimodality in vivo imaging. *Proc Natl Acad Sci USA* 104, 15549-15554 (2007).
13. Heidel, J. D., et al. Potent siRNA inhibitors of ribonucleotide reductase subunit RRM2 reduce cell proliferation in vitro and in vivo. *Clin Cancer Res* 13, 2207-2215 (2007).
14. Heidel, J. D., et al. Administration in non-human primates of escalating intravenous doses of targeted nanoparticles containing ribonucleotide reductase subunit M2 siRNA. *Proc Natl Acad Sci USA* 104, 5715-5721 (2007).
15. Ribas, A., Kalinoski, L., Heidel, J D., Peterkin, J., Seligson, D B., Zuckerman, J E., Choi, C., Yen, Y., Davis, M E., Tolcher, A W. Systemic delivery of siRNA via targeted nanoparticles in patients with cancer: Results from a first-in-class phase I clinical trial. *Journal of Clinical Oncology* 28:15s, suppl; abstract 3022 (2010).
16. Aleku, M., et al. Atu027, a liposomal small interfering RNA formulation targeting protein kinase N3, inhibits cancer progression. *Cancer Res* 68, 9788-9798 (2008).
17. Santel, A., et al. Atu027 prevents pulmonary metastasis in experimental and spontaneous mouse metastasis models. *Clin Cancer Res* 16, 5469-5480.
18. Strumberg, D., Schultheis, B., Traugott, U., Vank, C., Santel, A., Keil, O., Giese, K., Kaufmann, J., Drevs, J. First-in-human phase I study of Atu027, a liposomal small interfering RNA formulations, targeting protein kinase N3 (PKN3) in patients with advanced solid tumors. *Journal of Clinical Oncology* 29, suppl; abstract 3057 (2011).
19. Strumberg, D., Schultheis, B., Meyer-Sabellek, W., Vank, C., Gebhardt, F., Santel, A., Keil, O., Giese, K., Kaurmann, J., Drevs, J. Antimetastatic activity of Atu027, a liposomal small interfering RNA formulation, targeting protein kinase N3 (PKN3): Final results of a phase I study in patients with advanced solid tumors. *Journal of Clinical Oncology* 30, suppl; abstract e13597 (2012).
20. Huang, L. & Liu, Y. In vivo delivery of RNAi with lipid-based nanoparticles. *Annu Rev Biomed Eng* 13, 507-530.
21. Huang, L., Sullenger, B. & Juliano, R. The role of carrier size in the pharmacodynamics of antisense and siRNA oligonucleotides. *J Drug Target* 18, 567-574.
22. Kakizawa, Y., Furukawa, S., Ishii, A. & Kataoka, K. Organic-inorganic hybrid-nanocarrier of siRNA constructing through the self-assembly of calcium phosphate and PEG-based block aniomer. *J Control Release* 111, 368-370 (2006).
23. Kakizawa, Y., Furukawa, S. & Kataoka, K. Block copolymer-coated calcium phosphate nanoparticles sensing intracellular environment for oligodeoxynucleotide and siRNA delivery. *J Control Release* 97, 345-356 (2004).
24. Li, J., Chen, Y. C., Tseng, Y. C., Mozumdar, S. & Huang, L. Biodegradable calcium phosphate nanoparticle with lipid coating for systemic siRNA delivery. *J Control Release* 142, 416-421.
25. Li, J., Yang, Y. & Huang, L. Calcium phosphate nanoparticles with an asymmetric lipid bilayer coating for siRNA delivery to the tumor. *J Control Release* 158, 108-114.
26. Pittella, F., et al. Pancreatic cancer therapy by systemic administration of VEGF siRNA contained in calcium phosphate/charge-conversional polymer hybrid nanoparticles. *J Control Release* 161, 868-874.
27. Pittella, F., et al. Enhanced endosomal escape of siRNA-incorporating hybrid nanoparticles from calcium phosphate and PEG-block charge-conversional polymer for efficient gene knockdown with negligible cytotoxicity. *Biomaterials* 32, 3106-3114.
28. Sokolova, V., Kovtun, A., Prymark, O., Meyer-Zaika, W., Kubareva, E A., Romanova, E A., Oretskaya, T S., Heumann, R., Epple, M. Functionalisation of calcium phosphate nanoparticles by oligonucleotides and their application for gene silencing. *Journal of Materials Chemistry* 17, 721-727 (2007).
29. Zhang, M., Ishii, A., Nishiyama, N., Matsumoto, S., Ishii, T., Yamasaki, Y., and Kataoka, K. PEGylated Calcium Phosphate Nanocomposites as Smart Environment-Sensitive Carriers for siRNA Delivery. *Advanced Materials* 21, 3520-3525 (2009).
30. Yang, Y., Hu, Y., Wang, Y., Li, J., Liu, F., Huang, L. Nanoparticle Delivery of Pooled siRNA for Effective Treatment of Non-small Cell Lung Cancer. *Molecular Pharmaceutics* (2012).
31. Yang, Y., Li, J., Liu, F., Huang, L. Systemic Delivery of siRNA via LCP Nanoparticle Efficiently Inhibits Lung Metastasis. *Molecular Pharmaceutics* 20, 609-615 (2012).
32. Elbashir, S. M., et al. Duplexes of 21-nucleotide RNAs mediate RNA interference in cultured mammalian cells. *Nature* 411, 494-498 (2001).
33. Elbashir, S. M., Lendeckel, W. & Tuschl, T. RNA interference is mediated by 21- and 22-nucleotide RNAs. *Genes Dev* 15, 188-200 (2001).
34. Choudhury, A., Charo, J., Parapuram, S K., Hunt, R C., Hunt D M., Seliger, B., Kiessling, R. Small Interfering RNA (siRNA) Inhibits the Expression of the Her2/Neu Gene, Upregulates HLA Class 1 and Induces Apoptosis of Her2/Neu Positive Tumor Cell Lines. *International Journal of Cancer* 108, 70-77 (2004).
35. Judge, A. D., et al. Confirming the RNAi-mediated mechanism of action of siRNA-based cancer therapeutics in mice. *J Clin Invest* 119, 661-673 (2009).
36. Tran, M. A., et al. Targeting V600EB-Raf and Akt3 using nanoliposomal-small interfering RNA inhibits cutaneous melanocytic lesion development. *Cancer Res* 68, 7638-7649 (2008).

We claim:

1. Non-lipid, non-toxic, and non-aggregating nanoparticles comprising $Ca_wPO_{4x}R_yS_z$ where w is from 90 to 125, x is from 75 to 95, y is from 1 to 6, and z is from 0 to 6, where R is a double-stranded oligonucleotide between 15-31 base pairs in length or a single stranded oligonucleotide between 15-31 base pairs in length, and where S is polyethylene glycol or a surface modifier, stabilizing agent or a combination thereof capable of being conjugated to R if z>0
   wherein the size of the resulting nanoparticles within a specified concentration range and molar ratio of calcium and phosphate is determined by the concentration and size of the oligonucleotide.

2. A nanoparticle of claim 1 where R is selected from the group consisting of ribonucleic acid, deoxyribonucleic acid, or derivatives thereof.

3. A nanoparticle of claim 1 where R is either blunt-ended or contains 3' nucleotide overhangs.

4. A nanoparticle of claim 1 where R contains an active group on the 5' or 3' end comprising amine, carboxy, sulfhydryl, phosphate, maleimide or other groups that can be covalently bonded to S.

5. A nanoparticle of claim 1 where R contains either no modification, 2'O-methoxy modification or other chemical modification on the base structures.

6. A nanoparticle of claim 1 where S is a polyethylene glycol containing amine, carboxy, sulfhydryl, methoxy or methyl terminal groups or other covalently bonded groups that can be used to create a bond with an active group on the R molecule.

7. A nanoparticle of claim 6 where S ranges in size from 500 Da to 20 kDa.

8. A nanoparticle of claim 1 where R is conjugated to S via a phosphoamide, amide, disulfide, thioether or other chemical bond.

9. A nanoparticle of claim 1 where both unconjugated R and S and conjugated R-S are incorporated.

10. A nanoparticle of claim 1 where the total incorporated Ca:R molar ratio ranges from 25-100 for 25 bp, more optimally from 41.67-62.50 for 25 bp and 18.18-33.33 for 21 bp and more optimally 22.22-28.57 for 21 bp.

11. A nanoparticle of claim 1 where the Ca:P molar ratio is 0.9 to 1.67, more optimally 1.1 to 1.3 and most optimally 1.2.

12. A nanoparticle of claim 1 where the nanoparticle is suspended in an aqueous dispersion having a pH of 5 to 12, more optimally 6 to 8.

13. A nanoparticle of claim 1 where the nanoparticle has a particle size ranging from 10 nm-1 um, more optimally 10 nm-200 nm, and most optimally 100 nm-120 nm.

14. A nanoparticle of claim 1 where the nanoparticle is further modified by incubation with $CaCl_2$ with heat.

15. A nanoparticle of claim 1 in which R is a small interfering RNA (siRNA).

16. A nanoparticle of claim 1 in which R may be multiple different oligonucleotide sequences.

17. A nanoparticle of claim 15 where R is siRNA sequence PI3KCA (SEQ ID NOS 1 and 2).

18. A nanoparticle of claim 15 where R is siRNA sequence PI3KCA-3140 A>G mutation (SEQ ID NOS 3 and 4).

19. A nanoparticle of claim 15 where R is siRNA sequence PI3KCA-3140 A>G mutation (SEQ ID NOS 5 and 6).

20. A nanoparticle of claim 15 where R is siRNA sequence PI3KCA-1633 G>A mutation (SEQ ID NOS 7 and 8).

21. A nanoparticle of claim 15 where R is siRNA sequence PI3KCA-333 G>C mutation (SEQ ID NOS 9 and 10).

22. A nanoparticle of claim 15 where R is siRNA sequence HER2 (as published[34]) (SEQ ID NOS 11 and 12).

23. A nanoparticle of claim 15 where R is siRNA sequence HER2 (SEQ ID NOS 13 and 14).

24. A nanoparticle of claim 15 where R is siRNA sequence PLK (SEQ ID NOS 15 and 16).

25. A nanoparticle of claim 15 where R is siRNA sequence BRAF-V600E mutation (SEQ ID NOS 19 and 20).

* * * * *

SEQUENCE LISTING

<160> NUMBER OF SEQ ID NOS: 22

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
aucgauaagc ugucgcacgg uuaga                                        25

<210> SEQ ID NO 2
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ucuaaccgug cgacagcuua ucgag                                        25

<210> SEQ ID NO 3
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3

-continued aaaugaauga ugcacgucau ggugg                                        25

<210> SEQ ID NO 4
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
accaugacgu gcaucauuca uuugu                                        25

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gucauggugg cuggacaaca a                                            21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
guuguccagc caccaugaag u                                            21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cucucugaaa ucacuaagcu u                                            21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gcuuagugau uucagagauu u                                            21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
caaccgugaa gaaaacaucu u                                             21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gauguuuucu ucacgguagu u                                             21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ucucugcggu gguuggcauu c                                             21

<210> SEQ ID NO 12
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
accaugacgu gcaucauuca uuugu                                         25

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
uuccgaaaga gcuggucccu u                                             21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gggaccagcu cuuucggaau u                                             21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
uauuuaagga gggugaucuu u                                             21

```
<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
agaucacccu ccuuaaauau u                                            21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
uacauaaccg gacauaaucu u                                            21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gauuaugucc gguuauguau u                                            21

<210> SEQ ID NO 19
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ggucuagcua cagagaaauc ucgau                                        25

<210> SEQ ID NO 20
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
cgagauuucu cuguagcuag accau                                        25

<210> SEQ ID NO 21
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
aauucuccga acgugucacg ugaga                                        25
```

```
<210> SEQ ID NO 22
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ucucacguga cacguucgga gaauu                                          25
```